United States Patent [19]

Helling

[11] Patent Number: 4,921,782
[45] Date of Patent: May 1, 1990

[54] MAGENTA COUPLER MONOMER, A POLYMERIC MAGENTA COUPLER AND A COLOR PHOTOGRAPHIC RECORDING MATERIAL CONTAINING THE POLYMERIC MAGENTA COUPLER

[75] Inventor: Günter Helling, Odenthal-Gloebusch, Fed. Rep. of Germany

[73] Assignee: Agfa-Gevaert Aktiengesellschaft, Leverkusen, Fed. Rep. of Germany

[21] Appl. No.: 200,541

[22] Filed: May 31, 1988

[30] Foreign Application Priority Data

Jun. 11, 1987 [DE] Fed. Rep. of Germany ....... 3719401
Jul. 8, 1987 [DE] Fed. Rep. of Germany ....... 3722497

[51] Int. Cl.$^5$ ............................................. G03C 7/38
[52] U.S. Cl. .................................... 430/548; 430/558
[58] Field of Search ................................. 430/548, 558

[56] References Cited

U.S. PATENT DOCUMENTS 4,576,910  3/1986  Hirano et al. ...................... 430/548
4,585,732  4/1986  Kawagishi et al. ................. 430/548
4,769,313  9/1988  Fujimoto et al. ................... 430/548

Primary Examiner—Richard L. Schilling
Assistant Examiner—Mark R. Buscher
Attorney, Agent, or Firm—Connolly and Hutz

[57] ABSTRACT

Polymeric magenta couplers containing polymerized units of a carboxyl-containing polymerizable pyrazoloazole coupler corresponding to formula I below give magenta images characterized increased color density Dmax.

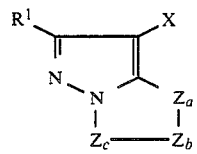

in this formula, $R^1$=H, alkyl, aralkyl or aryl; X=H or a group releasable by coupling; $Z_a$, $Z_b$, $Z_c$=an optionally substituted methine group, =N— or —NH—, either the bond $Z_a$—$Z_b$ or the bond $Z_b$—$Z_c$ being a double bond and the other bond being a single bond; and at least $R^1$ or X or a substituent at a methine group $Z_a$, $Z_b$ or $Z_c$ contains an ethylenically unsaturated polymerizable group in optionally polymerized form and at least $R^1$ or X or a substituent at a methine group $Z_a$, $Z_b$ or $Z_c$ contains a carboxyl group.

3 Claims, No Drawings

MAGENTA COUPLER MONOMER, A POLYMERIC MAGENTA COUPLER AND A COLOR PHOTOGRAPHIC RECORDING MATERIAL CONTAINING THE POLYMERIC MAGENTA COUPLER

This invention relates to a new magenta coupler monomer, to a polymeric magenta coupler obtained therefrom and to a color photographic recording material containing this polymeric magenta coupler. The polymeric magenta coupler is obtained by polymerization of ethylenically unsaturated monomers and contains pyrazoloazole groups and acid groups.

It is known that colored photographic images can be produced by chromogenic development, i.e. by developing silver halide emulsion layers which have been exposed to form an image in the presence of suitable color couplers using suitable dye-producing developer substances (so-called color developers), the oxidation product of the developer substances formed in correspondence with the silver image reacting with the color coupler to form a dye image. The color couplers used are normally aromatic compounds containing primary amino groups, particularly those of the p-phenylenediamine type.

It is known that the color couplers may be used in the form of polymer dispersions in which the functional group of a color coupler is attached once or several times to a polymer structure and, in this way, is made resistant to diffusion. Accordingly, a polymer such as this contains recurring structural units with the color coupler.

Color couplers which are incorporated in the layers of photographic recording materials in the form of polymer dispersions of the type in question generally show adequate resistance to diffusion and do not significantly affect the mechanical properties of the layers, even with low binder contents. It is particularly important that they do not crystallize out during storage, show high stability to light, heat and moisture and that the dyes produced from them are stable, show the desired spectral properties and are resistant to diffusion during development and are deposited in the form of as fine a grain as possible. Color couplers which are incorporated in photographic recording materials in the form of such polymer dispersions having a molecular weight above 5,000 generally show good colloidal stability and satisfy some of the above-mentioned requirements made of them extremely well. High molecular weight color couplers such as these are described, for example, in DE-C-1 297 417, DE-A-24 07 569, DE-A-31 48 125, DE-A-32 17 200, DE-A-33 20 079, DE-A-33 24 932 DE-A-33 31 743, DE-A-33 40 376, DE-A-34 61 455, EP-A-27 284, U.S. Pat. No. 4,080,211.

The high molecular weight color couplers are generally prepared by polymerization of ethylenically unsaturated, so-called monomeric color couplers.

However, the known polymeric magenta couplers have the following disadvantages:

The magenta dyes obtained from polymeric pyrazolone couplers do not show an ideal absorption. The yellow secondary density is particularly troublesome, necessitating the additional use of masking couplers.

Polymeric pyrazoloazole couplers, such as for example the compounds M-23 to M-27 from DE-A-35 16 996 or compound XV from EP-A-0 133 262 and also the compounds from U.S. Pat. No. 4,576,910, give a total inadequate dye yield and, for this reason, are unuseable.

The object of the present invention is to provide improved polymeric magenta couplers for color photographic recording materials.

The present invention relates to magenta couplers containing at least one structural unit capable of color coupling corresponding to the following formula

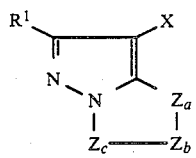

I in which $R^1$ is H, alkyl, aralkyl or aryl;

X is H or a group releasable by coupling;

$Z_a$, $Z_b$, $Z_c$ represent an optionally substituted methine group, =N— or —NH—, either the bond $Z_a$—$Z_b$ or the bond $Z_b$—$Z_c$ being a double bond and the other bond a single bond;

and in which at least $R^1$ or X or a substituent at a methine group represented by $Z_a$, $Z_b$ or $Z_c$ contains an ethylenically unsaturated polymerizable group in optionally polymerized form, characterized in that at least $R^1$ or X or a substituent at a methine group represented by $Z_a$, $Z_b$ or $Z_c$ contains a carboxyl group.

The magenta couplers corresponding to formula I may be both low molecular weight polymerizable coupler monomers (hereinafter referred to as coupler-containing monomer K) and also polymeric color couplers obtained by polymerization of the monomers (hereinafter referred to as polymer coupler P). In the first case, the ethylenically unsaturated polymerizable group mentioned is still present as such; in the second case, it is incorporated by polymerization in a polymer chain, the polymer formed bearing the couplable pyrazoloazole groups as side groups. In either case, at least one carboxyl group is present per couplable group.

The coupler-containing monomer K corresponds to the following general formula

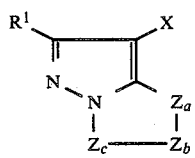

I in which $R^1$ is H, alkyl, aralkyl or aryl;

X is H or a group releasable by coupling;

$Z_a$, $Z_b$, $Z_c$ represent an optionally substituted methine group, =N— or —NH—, either the bond $Z_a$—$Z_b$ or the bond $Z_b$—$Z_c$ being a double bond and the other bond a single bond;

and in which at least $R^1$ or X or a substituent at a methine group represented by $Z_a$, $Z_b$ or $Z_c$ contains an ethylenically unsaturated polymerizable group corresponding to the following formula

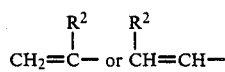

in which

R² is H, halogen, particularly chlorine, —COOH or alkyl, preferably containing 1 to 4 carbon atoms and optionally substituted by —COOH; and in which at least R¹ or X or a substituent at a methine group represented by $Z_a$, $Z_b$ or $Z_c$ contains a carboxyl group. The carboxyl group is preferably situated at the same substituent which also contains the polymerizable group.

An alkyl, aralkyl or aryl group represented by R¹ may be substituted, for example by halogen, alkoxy, aroxy, acylamino and (for example in the case of aryl) by alkyl and, in addition, may contain—optionally through such substituents—the already mentioned ethylenically unsaturated polymerizable group and, optionally, also a carboxyl group.

A substituted methine group represented by $Z_a$, $Z_b$ or $Z_c$ corresponds to the following formula

in which R³ represents alkyl containing up to 18 carbon atoms, aryl, aralkyl, a heterocyclic aromatic group, alkoxy, amino, a carbonamido group or —OH; the alkyl, aralkyl or aryl groups mentioned in particular may be further substituted and, optionally through such substituents, may contain the already mentioned ethylenically unsaturated polymerizable group and/or the carboxyl group.

The releasable group X is, for example, a halogen atom, for example Cl, or an organic group which is generally attached to the coupling position of the coupler molecule by an oxygen, sulfur or nitrogen atom. Where the releasable group is a cyclic group, it may be attached to the coupling position of the coupler molecule either directly by an atom which is part of a ring, for example a nitrogen atom, or indirectly through an intermediate bond. Releasable groups such as these are known in large numbers, for example as leaving groups of 2-equivalent magenta couplers.

Examples of releasable groups attached by oxygen correspond to the following formula

in which R⁴ is an acyclic or cyclic organic radical, for example alkyl, aryl, a heterocyclic group or acyl, which is derived for example from an organic carboxylic or sulfonic acid. In particularly preferred releasable groups of this type, R⁴ is an optionally substituted phenyl group.

Examples of releasable groups attached by nitrogen can be found in the following German published specifications (DE-A-): 25 36 191, 27 03 589, 28 13 522, 33 39 201.

The rings in question are often 5-membered heterocyclic rings which are attached to the coupling position of the magenta coupler by a ring nitrogen atom. The heterocyclic rings often contain activating groups, for example carbonyl or sulfonyl groups, or double bonds adjacent the nitrogen atom establishing the bond to the coupler molecule.

Where the releasable group is attached to the coupling position of the coupler by a sulfur atom, it may be the residue of a diffusible mercapto compound which is capable of inhibiting the development of silver halide. Inhibitor residues such as these have frequently been described as releasable groups attached to the coupling position of couplers, including magenta couplers, for example in U.S. Pat. No. 3,227,554.

The releasable group X may also contain the ethylenically unsaturated polymerizable group mentioned, as described for example in Research Disclosure 25724 (Sept. 1985). The releasable group X may also contain a carboxyl group.

Examples of coupler-containing monomers C correspond to formulae II to VI below:

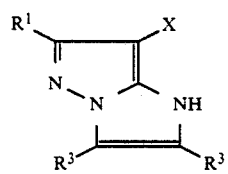

II

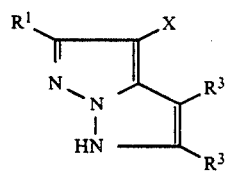

III

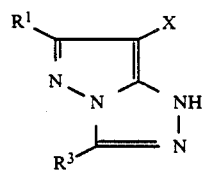

IV

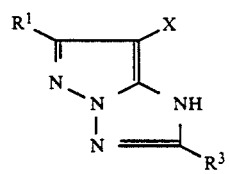

V

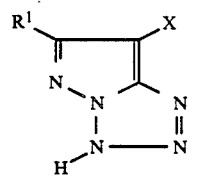

VI in which X, R¹ and R³ are as already defined, although two substiutents R³ in the same formula (II, III) are not necessarily identical and at least one of the substituents R¹, R³ and X in each of formulae II to VI containing an ethylenically unsaturated polymerizable group and at least one of the substituents R¹, R³ and X a carboxyl group. Monomers corresponding to formula IV are preferred.

The ethylenically unsaturated group may be attached to one of the two heterocyclic rings corresponding to any of formulae II to VI either directly or indirectly through a bond L. The bond —L— may have a composite structure and may be represented, for example, as follows:

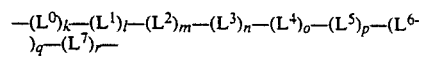

in which L⁰ represents that part of the bond situated adjacent the heterocyclic ring while L⁷ represents that part of the bond situated adjacent the ethylenically unsaturated group and in which $L^0$, $L^2$, $L^4$, $L^6$ (same or different) represent —O—, —NR—, —NRCO—, —CONR—, —NRSO$_2$—, —SO$_2$NR—, —COO—, —O—CO—, —N-R—CO—NR—, —O—CO—NR—, —NR—COO— (with R=H or alkyl optionally substituted by carboxyl);

$L^1$, $L^3$, $L^5$, $L^7$ (same or different) represent alkylene, aralkylene, arylene, optionally substituted by carboxy;

k, l, m, n, o, p, q, r are each 0 or 1 with $1-m+n-o+p-q=0$.

An alkylene group represented by $L^1$, $L^3$, $L^5$, $L^7$ may be linear or branched, may contain up to 20 carbon atoms and may optionally be substituted by carboxyl.

An aralkylene group represented by $L^1$, $L^3$, $L^5$ is one of the following groups for example:

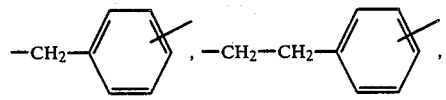

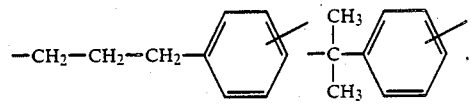

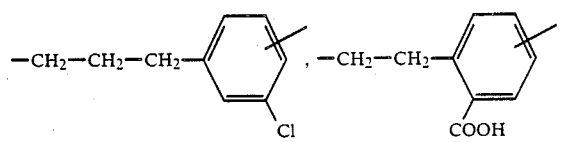

An a arylene group represented by $L^1$, $L^3$, $L^5$, $L^7$ is preferably a phenylene group which may be substituted, for example by alkyl, alkoxy, halogen, acylamino, carboxyl or a substituent containing a carboxyl group.

The following are examples of suitable coupler-containing monomers C:

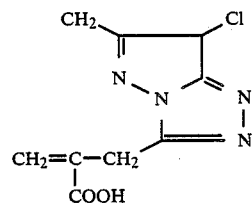

C-1

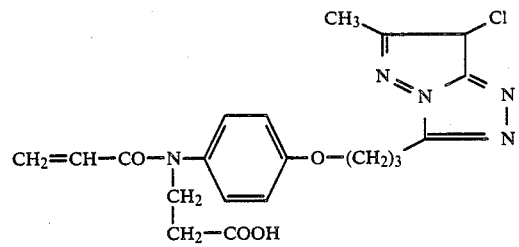

C-2

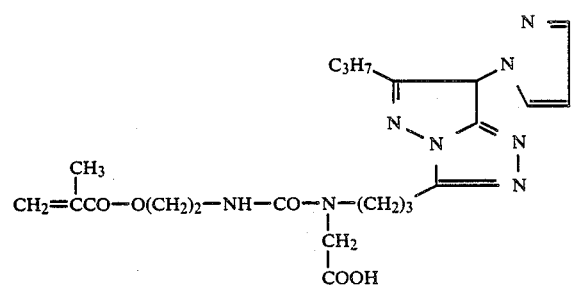

C-3

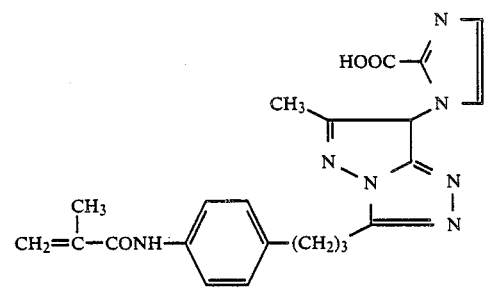

C-4

-continued
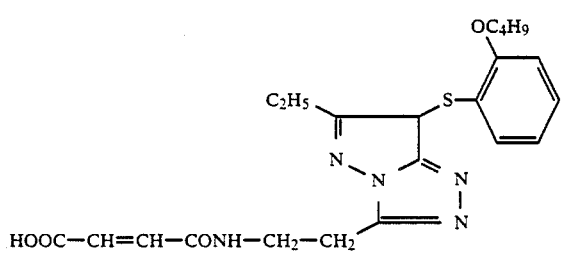
C-5
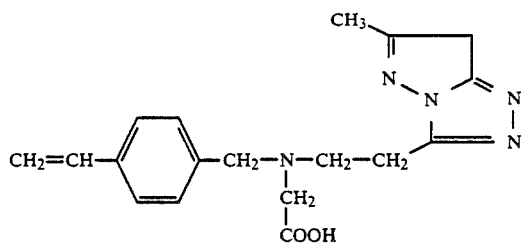
C-6
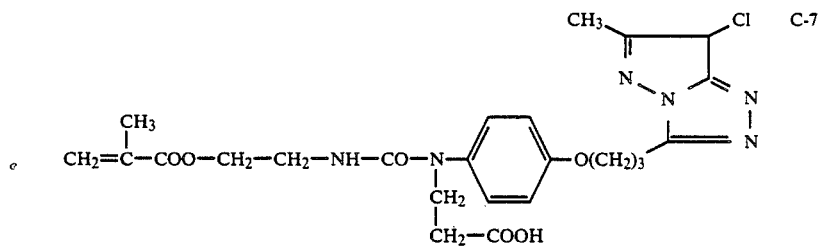
C-7
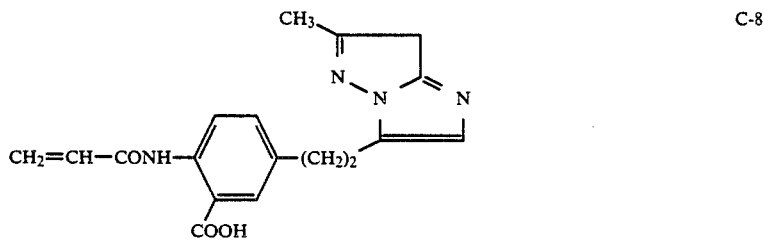
C-8
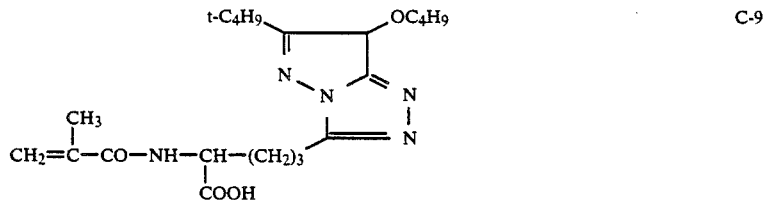
C-9
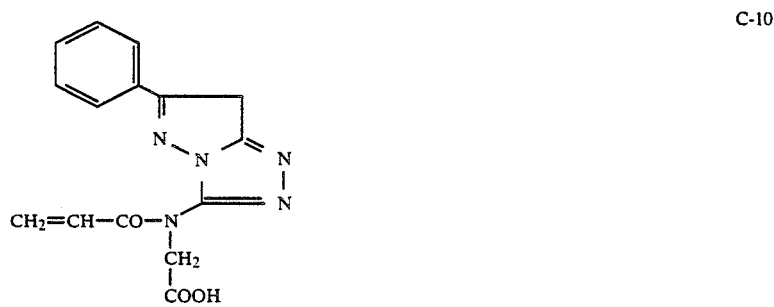
C-10

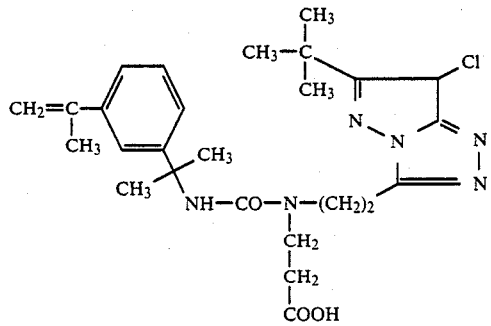

C-11

The polymeric color couplers according to the invention are obtained by polymerization from the coupler-containing monomers C, optionally in the presence of other polymerizable comonomers. They contain at least 20% by weight of polymerized units corresponding to formula I, i.e. the coupler-containing monomer C generally makes up from 20 to 100% by weight and preferably from 30 to 70% by weight of the polymeric color couplers.

Accordingly, in addition to the recurring units of coupler-containing monomer C, the polymeric couplers according to the invention may contain recurring units of at least one other copolymerized monomer CM. Examples of such monomers CM include esters and amides of acrylic acid and derivatives thereof, for example of acrylic acid, α-chloroacrylic acid, methacrylic acid (for example acrylamide, methyl methacrylate, ethyl acrylate, ethyl methacrylate, n-propyl acrylate, n-butyl acrylate, 2-ethylhexyl acrylate, n-hexyl acrylate, octyl methacrylate, lauryl methacrylate and methylene-bis-acrylamide), vinyl esters (for example vinyl acetate, vinyl propionate and vinyl laurate), acrylonitrile, methacrylonitrile, aromatic vinyl compounds (for example styrene, vinyl toluene, divinylbenzene, vinyl acetophenone, styrene sulfonic acid), itaconic acid, citraconic acid, crotonic acid, acrylic acid, methacrylic acid, vinylidene chloride, vinylalkyl ethers (for example vinylethyl ether), esters of maleic acid, N-vinyl-2-pyrrolidone, N-vinyl-, 2-vinyl- and 4-vinyl pyridine. The monomer CM may make up from 0 to 80% by weight and preferably from 30 to 70% by weight of the polymeric color coupler.

It is particularly preferred to use an ester of acrylic or methacrylic acid and/or an aromatic vinyl compound as the monomer CM. Two or more of the above-described monomers CM may optionally be used at the same time. For example, it is possible, in addition to the monomer C, to use a combination of n-butyl acrylate and divinylbenzene, styrene and methyl methacrylate, methyl acrylate and butyl methacrylate. The ethylenically unsaturated monomer CM may be selected to have a favorable effect on the physical properties and/or chemical properties of the copolymer to be prepared, for example its solubility, compatibility with a binder, such as gelatin, or other photographic additives, such as dye-producing compounds, UV-absorbers, antioxidants and the like, and on the flexibility of the layer compositions or rather the color photographic recording materials. Although the monomers CM generally contain no photographically active groups, it is also possible to use as the monomer CM compounds which, in addition to the ethylenically unsaturated polymerizable group, contain a photographically active group, for example a couplable group, but not the coupler group shown in formula I. Couplable groups such as these may have the properties of white couplers or masking couplers for example or may release a photographically active group, for example an inhibitor or development accelerator, during the coupling reaction.

The polymers according to the invention preferably have molecular weights above 5,000 and, more preferably, above 20,000. The upper limit is not critical and may be above 10,000,000, particularly where bifunctional or polyfunctional monomers are used as the additional monomer CM.

The polymeric magenta couplers according to the invention are generally added to the color photographic recording materials in the form of polymer dispersions, for example as a polymer latex.

The polymerization of the monomer C according to the invention or of the monomer mixture (monomer C and monomer CM) may be carried out by any of the usual polymerization processes, for example by emulsion polymerization or by polymerization in an organic solvent.

The polymerization of the ethylenically unsaturated monomers is generally initiated by free radicals which are formed by thermal decomposition of a chemical initiator, by the action of a reducing agent on an oxidizing compound (redox initiator) or by a physical effect, such as irradiation with ultra-violet rays or other high-energy radiation, high frequencies, etc.

Examples of chemical initiators include a persulfate (for example ammonium persulfate or potassium persulfate, etc.), a peroxide (for example hydrogen peroxide, benzoyl peroxide or tert.-butyl peroctoate, an azonitrile compound (for example 4,4'-azo-bis-4-cyanovaleric acid or azobisisobutyronitrile) or an azo ester (for example 2,2'-azobis(methylisobutyrate)).

Examples of conventional redox initiators include hydrogen peroxide-iron(II) salt, potassium persulfate, sodium metabisulfite and cerium(IV) salt-alcohol.

Examples of initiators and their functions are described by F. A. Bovey in "Emulsion Polymerization", Interscience Publishers Inc., NY, 1955, pages 59 to 93.

The emulsifier used for emulsion polymerization is a surfactant. Preferred examples of surfactants include soaps, sulfonates, sulfates, cationic compounds, amphoteric compounds and high molecular weight protective colloids. Special examples of the emulsifiers and their functions are described in Belgische Chemische Industrie, Vol. 28, pages 16 to 20, 1963.

Any organic solvent used in the preparation of the polymer or during dispersion of the polymer in an aqueous gelatin solution may be removed from the casting solution before casting.

Suitable solvents are, for example, those which show a certain solubility in water, so that they may readily be removed by washing with water in a gelatin noodle state and those which may be removed by spray-drying, vacuum or steam rinsing.

Examples of solvents such as these include esters (for example ethyl acetate), ethers, ketones, halogenated hydrocarbons (for example methylene chloride, trichloroethylene), alcohols (for example methanol, ethanol, butanol) and combinations thereof.

To improve the stability of the dispersion and the flexibility of the emulsion layered thereon, it is possible to add a small quantity (preferably no more than 50% by weight, based on the polymeric coupler according to the invention) of a permanent solvent, more especially a water-immiscible high-boiling organic solvent, for example dibutylphthalate and/or tricresyl phosphate. The concentration of the permanent solvent should be high enough to plasticize the polymer while it is kept in the state of a solid particle. On the other hand, the concentration of the permanent solvent should be as low as possible in the interests of minimal layer thickness.

Some representative Examples of the synthesis of the magenta couplers according to the invention are given in the following.

Monomer C-2

23 g 3-[3-(4-aminophenoxy)-propyl]-6-methyl-7-chloro-1H-pyrazolo[5,1-c]-1,2,4-triazole and 10.8 g acrylic acid are dissolved in dimethyl acetamide heated to 85° C. and are stirred at that temperature for 1 hour. The reaction mixture is then poured onto 300 g of an ice/water mixture, the deposit precipitated is filtered off under suction and recrystallized from ethyl acetate. 3-[3-(4-carboxyethylaminophenoxy)-propyl]-6-methyl-7-chloro-1H-pyrazolo-[5,1-c]-1,2,4-triazole melting at 151° to 153° C. is obtained in a yield of 61%.

23 g of this product and 4.0 g N,N-dimethyl aniline are dissolved in 100 ml dimethylacetamide and the resulting solution cooled to −12° C. A solution of 3.2 g acrylic acid chloride dissolved in 10 ml dimethyl acetamide is then added dropwise, followed by stirring for 30 minutes at 10° C. The reaction mixture is then introduced into 700 g of an ice/water mixture, 20 ml of a concentrated hydrochloric acid added and the deposit formed filtered off under suction. The crude product obtained is recrystallized from ethyl acetate. The monomer C-2 which has a melting point of 175° C. is obtained in a yield of 60%.

Monomer C-7

13 g 3-[3-(4-carboxyethylaminophenoxy)-propyl]-6-methyl-7-chloro-1H-pyrazolo-[5,1-c]-1,2,4-triazole (see preparation of monomer C-2) were dissolved in 50 ml anhydrous pyridine and 0.16 g di-tert.-butylphenol added to the resulting solution. 5.3 g isocyanatoethyl methacrylate were then added dropwise at 25° C. After stirring for 30 minutes, the product was precipitated by stirring into ligroin, filtered under suction, washed with petroleum ether and dissolved in methanol.

Polymer coupler P-1

Copolymer of monomer C-2 and ethyl acrylate

A solution of 2.1 g oleyl methyl tauride in 49 g water was heated under nitrogen to 80° C. 4.05 g ethyl acrylate and 0.94 g of a 4.3% solution of azo-bis-cyanovaleric acid in methanol were added to the resulting solution with stirring, followed by stirring for 1 hour at 80° C. A heated solution of 22.95 g ethyl acrylate and 18 g monomer C-2 in 204.3 ml methanol and 9.5 g of a 4.3% solution of azo-biscyanovaleric acid in methanol were then added dropwise over a period of 1 hour. After stirring for another 2 hours at 80° C., the methanol was evaporated off from the reaction mixture and the latex obtained filtered. A finely divided latex coupler having a solids content of 10.6% was obtained.

Polymer coupler P-2

Copolymer of monomer C-7 and butyl acrylate

A solution of 0.63 g oleyl methyl tauride in 121 g water was heated under nitrogen to 80° C. 1.4 g butyl acrylate and 0.33 g of a 4.3% solution of azo-bis-cyanovaleric acid in methanol were added to the resulting solution, followed by stirring for 1 hour at 80° C. A mixture of 8 g butyl acrylate, 36.3 ml methanol and 23.2 g of a 17.3% solution of C-7 in methanol and 2.8 g of a 4.3% solution of azo-bis-cyanovaleric acid in methanol were then added to the reaction solution After stirring for 2 hours at 80° C., the methanol was separated off by distillation. A finely divided latex coupler was obtained. Solids content: 12.0%.

Polymer coupler P-3

Copolymer of monomer C-2 and butyl acrylate

This coupler was prepared in the same way as polymer coupler P-1, except that butyl acrylate was used instead of ethyl acrylate and an aqueous potassium peroxydisulfate solution was used instead of the methanolic azo-bis-cyanovaleric acid. A finely divided latex coupler having a solids content of 12.6% was obtained.

Polymer couplers P-4 to P-15

Using the coupler-containing monomers C described above, the polymer couplers described in Table 1 below were prepared in the same way as the copolymers in the foregoing Examples.

The following abbreviations are used for the comonomers CM:
BA butyl acrylate
EA ethyl acrylate
EHA ethyl hexyl acrylate
MA methyl acrylate
BM butyl methacrylate
PPA i-propyl acrylamide
AMPS 2-acrylamido-2-methyl propanesulfonic acid

TABLE 1

| Polymer coupler | Monomer C | % by weight | Monomer CM | % by weight |
|---|---|---|---|---|
| P-4 | C-2 | 60 | BM | 40 |
| P-5 | C-2 | 50 | MA/BA 1:1 | 50 |
| P-6 | C-3 | 40 | BA | 60 |
| P-7 | C-3 | 30 | EHA | 70 |
| P-8 | C-7 | 60 | BA | 40 |
| P-9 | C-7 | 50 | BA/PPA 8:2 | 50 |
| P-10 | C-7 | 55 | EA | 45 |
| P-11 | C-8 | 30 | EA | 70 |
| P-12 | C-11 | 40 | BA | 60 |
| P-13 | C-11 | 70 | BA | 30 |
| P-14 | C-8 | 50 | BA/AMPS 9:1 | 50 |
| P-15 | C-9 | 50 | BA | 50 |

The color photographic recording material according to the invention comprises at least one photosensitive silver halide emulsion layer and, preferably, a sequence of several such photosensitive silver halide emulsion layers and, optionally, non-photosensitive binder layers arranged in between, a polymeric magenta coupler according to the present invention being associated with at least one of the photosensitive silver halide emulsion layers present.

The photosensitive silver halide emulsions used in the photosensitive layers may contain chloride, bromide and iodide or mixtures thereof as halide. For example, 0 to 12 mol % of the halide of at least one layer may consist of iodide, 0 to 50 mol % of chloride and 50 to 100 mol % of bromide. In certain embodiments, the crystals are predominantly compact crystals which are, for example, cubic or octahedral or have transitional forms. They may be characterized by the fact that they mostly have a thickness of greater than 0.2 μm. The average ratio of diameter to thickness is preferably less than 8:1, the diameter of a crystal being defined as the diameter of a circle with an area corresponding to the projected area of the crystal. In other embodiments, however, all the emulsions or individual emulsions may even contain substantially tablet-form silver halide crystals in which the ratio of diameter to thickness is greater than 8:1. The emulsions may be heterodisperse or even monodisperse emulsions which preferably have a mean grain size of from 0.3 μm to 1.2 μm. The silver halide grains may even have a layered grain structure.

The emulsions may be chemically and/or spectrally sensitized in the usual way. They may also be stabilized by suitable additives. Suitable chemical sensitizers, spectral sensitizing dyes and stabilizers are described, for example, in Research Disclosure 17643; cf. in particular Chapters III, IV and VI.

The color photographic recording material according to the invention preferably contains at least one silver halide emulsion layer for recording light of each of the three spectral regions red, green and blue. To this end, the photosensitive layers are spectrally sensitized in known manner by suitable sensitizing dyes. Blue-sensitive silver halide emulsion layers do not necessarily have to contain a spectral sensitizer, because in many cases the natural sensitivity of the silver halide is sufficient for recording blue light.

Each of the photosensitive layers mentioned may consist of a single layer or, in known manner, for example as in the so-called double layer arrangement, may also comprise two or more partial silver halide emulsion layers (DE-C-1 121 470). Normally, red-sensitive silver halide emulsion layers are arranged nearer the layer support than green-sensitive silver halide emulsion layers which in turn are arranged nearer than blue-sensitive emulsion layers, a non-photosensitive yellow filter layer generally being arranged between the green-sensitive layers and blue-sensitive layers. However, other arrangements are also possible. A non-photosensitive intermediate layer, which may contain agents to prevent the unwanted diffusion of developer oxidation products, is generally arranged between layers of different spectral sensitivity. Where several silver halide emulsion layers of the same spectral sensitivity are present, they may be arranged immediately adjacent one another or in such a way that a photosensitive layer of different spectral sensitivity is present between them (DE-A-1 958 709, DE-A-2 530 645, DE-A-2 622 922).

Color photographic recording materials according to the invention normally contain color couplers for producing the different component dye images cyan, magenta and yellow in spatial and spectral association with the silver halide emulsion layers of different spectral sensitivity, the polymeric couplers according to the present invention generally being associated with a green-sensitive silver halide emulsion layer.

In the context of the invention, spatial association means that the color coupler is present in such a spatial relationship to the silver halide emulsion layer that the two are capable of interacting in such a way as to allow imagewise accordance between the silver image formed during development and the dye image produced from the color coupler. This result is generally achieved by the fact that the color coupler is contained in the silver halide emulsion layer itself or in an adjacent, optionally non-photosensitive binder layer.

By spectral association is meant that the spectral sensitivity of each of the photosensitive silver halide emulsion layers and the color of the component dye image produced from the particular spatially associated color coupler bear a certain relationship to one another, a component dye image relating to another color (generally for example the colors cyan, magenta or yellow in that order) being associated with each of the spectral sensitivities (red, green, blue).

One or more color couplers may be associated with each of the differently spectrally sensitized silver halide emulsion layers. Where several silver halide emulsion layers of the same spectral sensitivity are present, each of them may contain a color coupler, the color couplers in question not necessarily having to be the same They are merely required to produce at least substantially the same color during color development, normally a color which is complementary to the color of the light to which the silver halide emulsion layers in question are predominantly sensitive.

In preferred embodiments, therefore, at least one non-diffusing color coupler for producing the cyan component dye image, generally a coupler of the phenol or α-naphthol type, is associated with red-sensitive silver halide emulsion layers. At least one non-diffusing color coupler for producing the magenta component dye image (for which purpose monomeric—low molecular weight—magenta couplers of the 5-pyrazolone, the indazolone or the pyrazoloazole type may optionally be used in addition to the polymeric magenta couplers according to the invention) is associated with green-sensitive silver halide emulsion layers. Finally, at least one non-diffusing color coupler for producing the yellow component dye image, generally a color coupler containing an open-chain ketomethylene group, is associated with blue-sensitive silver halide emulsion layers. Color couplers of this type are known in large numbers and are described in a number of patent specifications. Reference is made here, for example, to the publications entitled "Farbkuppler (Color Couplers)" by W. PELZ in "Mitteilungen aus den Forschungslaboratorien der Agfa, Leverkusen/München", Vol. III, page 111 (1961) and by K. VENKATARAMAN in "The Chemistry of Synthetic Dyes", Vol. 4, 341 to 387, Academic Press (1971).

The color couplers according to the invention and the other color couplers present in the color photographic recording material may be both standard 4-equivalent couplers and 2-equivalent couplers in which a smaller quantity of silver halide is required for dye production 2-equivalent couplers are known to be derived from the 4-equivalent couplers in that they contain in the coupling position a substituent which is eliminated during the coupling reaction. 2-Equivalent couplers include both those which are substantially colorless and also those which have a strong color of their own which either disappears during the color coupling reaction or is replaced by the color of the image dye produced. Couplers of the latter type may also be additionally present in the photosensitive silver halide emulsion layers where they serve as masking couplers for compensating the unwanted secondary densities of the image dyes. However, 2-equivalent couplers also include the known white couplers, although couplers such as these do not produce a dye on reaction with color developer oxidation products 2-equivalent couplers also include couplers which contain in the coupling position a releasable group which is released on reaction with color developer oxidation products and, in the process, develops a certain, desirable photographic activity, for example as a development inhibitor or accelerator. Examples of 2-equivalent couplers such as these are the known DIR couplers and also DAR and FAR couplers. The releasable group may also be a ballast group, so that coupling products, for example dyes, which are diffusible or which at least show slight or limited mobility are obtained during the reaction with color developer oxidation products.

By slight or limited mobility is meant a mobility which is gauged in such a way that the contours of the discrete dye patches formed during chromogenic development blend and merge with one another. This degree of mobility should be distinguished, on the one hand, from the usual case of complete immobility in photographic layers which, in conventional photographic recording materials, is required for the color couplers or rather for the dyes produced therefrom in order to obtain maximal definition and, on the other hand, from the case of total mobility of the dyes as required, for example, in dye diffusion processes. The last dyes mentioned generally contain at least one group which makes them soluble in the alkaline medium. The extent of the slight mobility required in accordance with the invention may be controlled by varying substituents in order, for example, specifically to influence solubility in the organic medium of the oil former or affinity for the binder matrix.

Suitable layer supports for the recording materials according to the invention are the usual types, for example supports of cellulose esters, for example cellulose acetate, and of polyesters Other suitable layer supports are paper supports which may optionally be coated, for example with polyolefins, particularly with polyethylene or polypropylene. Reference is made in this connection to Research Disclosure 17643, Chapter XVII.

Suitable protective colloids or binders for the layers of the recording material are the usual hydrophilic film-forming agents, for example proteins, particularly gelatin. Casting aids and plasticizers may be used, cf. Research Disclosure 17643, Chapters IX, XI and XII.

The layers of the photographic material may be hardened in the usual way, for example with hardeners containing at least two reactive oxirane, aziridine or acryloyl groups The layers may also be hardened by the process described in DE-A-22 18 009. The photographic layers or rather the color photographic multilayer materials may also be hardened with hardeners of the diazine, triazine or 1,2-dihydroquinoline series or with hardeners of the vinyl sulfone type. Other suitable hardeners are known from DE-A-24 39 551, DE-A-22 25 230, DE-A-22 17 672 and from Research Disclosure 17643, Chapter X.

Other suitable additives are described in Research Disclosure 17643 and in "Product Licensing Index" Dec., 1971, pages 107–110.

Suitable color developers for the material according to the invention are, in particular, those of the p-phenylenediamine type, for example 4-amino-N,N-diethyl aniline hydrochloride, 4-amino-3-methyl-N-ethyl-N-$\beta$-(methanesulfonamido)ethyl aniline sulfate hydrate, 4-amino-3-methyl-N-ethyl-N-$\beta$-hydroxyethyl aniline sulfate, 4-amino-N-ethyl-N-(2-methoxyethyl)-m-toluidine di-p-toluenesulfonic acid and N-ethyl-N-$\beta$-hydroxyethyl-p-phenylenediamine. Other suitable color developers are described, for example, in J. Amer. Chem. Soc. 73, 3100 (1951) and in G. Haist, Modern Photographic Processing, 1979, John Wiley and Sons, New York, pages 545 et seq.

After color development, the material is bleached and fixed in the usual way. Bleaching and fixing may be carried out separately or even together. Suitable bleaching agents are the usual compounds, for example $Fe^{3+}$ salts and $Fe^{3+}$ complex salts, such as ferricyanides, dichromates, water-soluble cobalt complexes, etc. Particular preference is attributed to iron(III) complexes of aminopolycarboxylic acids, more especially for example ethylenediamine tetraacetic acid, nitrilotriacetic acid, iminodiacetic acid, N-hydroxyethyl ethylenediamine triacetic acid, alkyliminodicarboxylic acids, and of corresponding phosphonic acids. Persulfates are also suitable bleaching agents.

EXAMPLE 1

The polymer couplers P-1, P-2, P-3, P-5, P-9 and P-10 according to the invention and the polymeric comparison couplers A and B were mixed with various samples of a silver halide emulsion which had been sensitized for green in accordance with the color coupler introduced. The silver halide gelatin emulsion used consisted of 75 g silver bromide iodide (iodide content 3 mol %) and 72 g gelatin, based on 1 kg emulsion.

The emulsions thus prepared were applied to a cellulose triacetate layer support provided with an adhesive layer and dried.

Photographic Testing

The individual samples were exposed by means of a sensitometer and then processed using the following color developer.

| Color developer | |
| --- | --- |
| Water, dist. | 800 g |
| Hydroxyethane diphosphonic acid, disodium salt | 2 g |
| Ethylenediamine tetraacetic acid, disodium salt | 2 g |
| Potassium carbonate | 34 g |
| Sodium hydrogen carbonate | 1.55 g |
| Sodium disulfite | 0.28 g |
| Sodium sulfite | 3.46 g |
| Potassium bromide | 1.34 g |
| Hydroxylamine sulfate | 2.4 g |
| N-ethyl-N-($\beta$-hydroxy)-ethyl-4-amino-3-ethyl aniline sulfate | 4.7 g |
| Water, dist. to 1000 ml | |

| Processing | Processing [mins] (25° C.) |
| --- | --- |
| Color developer | 10 |
| Stop bath | 4 |
| Intermediate rinse | 5 |
| Bleaching bath | 5 |
| Intermediate rinse | 5 |
| Fixing bath | 5 |

| -continued | |
|---|---|
| Final rinse | 10 |

The stop, bleaching and fixing baths are standard bath compositions. A formalin-free final bath was used.

The absorption maximum λmax and the maximum color density Dmax were determined (Table 2).

TABLE 2

| Polymer coupler | Dmax | λmax |
|---|---|---|
| A (comparison) | 0.62 | 545 |
| B (comparison) | 0.51 | 547 |
| 1 | 2.75 | 548 |
| 2 | 2.88 | 548 |
| 3 | 2.93 | 550 |
| 5 | 3.01 | 548 |
| 9 | 2.67 | 547 |
| 10 | 2.95 | 548 |

The results show that good maximal densities are only obtained with the latex couplers of the pyrazoloazole type according to the invention. The comparison polymers A and B are unuseable in practice on account of the poor color densities.

The pyrazoloazole polymers A and B were used as comparison coupler polymers (cf. U.S. Pat. No. 4,576,910 and EP-A No. 1 33 262).

Comparison polymer A

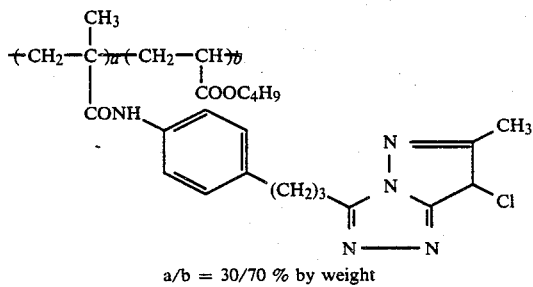

a/b = 30/70 % by weight

Comparison Example B

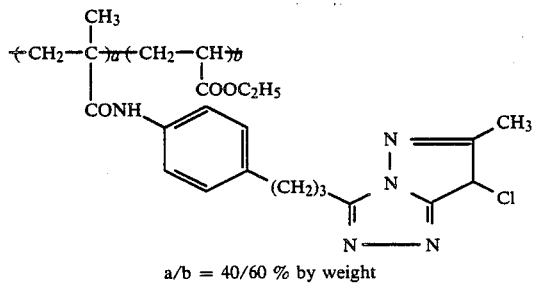

a/b = 40/60 % by weight

I claim:

1. A color photographic recording material comprising at least one photosensitive silver halide emulsion layer and at least one polymeric magenta coupler, said magenta coupler containing at least one structural unit capable of color coupling corresponding to the following formula

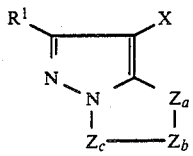

wherein $R^1$ is H, alkyl, aralkyl or aryl; X is H or a group releasable by coupling; $Z_a$, $Z_b$, $Z_c$ represent an optionally substituted methine group, $=N-$ or $-NH-$, either the bond $Z_a-Z_b$ or the bond $Z_b-Z_c$ being a double bond and the other bond a single bond; wherein at least $R^1$ or X or a substituent at a methine group represented by $Z_a$, $Z_b$ or $Z_c$ contains an ethylenically unsaturated polymerizable group in polymerized form, bonded to the coupler group through

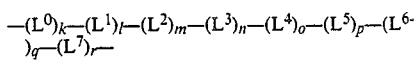

in which $L^0$ represents that part of the bond situated adjacent the coupler group while $L^7$ represents that part of the bond situated adjacent the ethylenically unsaturated group and in which $L^0$, $L^2$, $L^4$, $L^6$ (same or different) represent $-O-$, $-NR-$, $-NRCO-$, $-CONR-$, $-NRSO_2-$, $-SO_2NR-$, $-COO-$, $-O-CO-$, $-NR-CO-NR-$, $-O-CO-NR-$, $-NR-COO-$ (with R=H or alkyl optionally substituted by carboxyl); $L^1$, $L^3$, $L^5$, $L^7$ (same or different) represent alkylene, aralkylene, arylene, optionally substituted by carboxy; and k, l, m, n, o, p, q, r are each 0 or 1 with $1-m+n-o+p-q=0$; and wherein at least one of said $L^0$, $L^2$, $L^4$ and $L^6$ contains a nitrogen atom substituted with carboxy alkyl or at least one of the carbon atoms of said ethylenically unsaturated group is substituted with carboxyl or carboxy alkyl.

2. A color photographic recording material as claimed in claim 1 wherein said polymeric magenta coupler contains at least 20% by weight of polymerized structural units corresponding to formula I.

3. A color photographic recording material as claimed in claim 2 wherein said magenta coupler contains from 30 to 70% by weight of polymerized structural units of coupler monomers corresponding to the formula

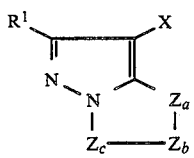

wherein $R^1$ is H, alkyl, aralkyl or aryl; X is H or a group releasable by coupling; $Z_a$, $Z_b$, $Z_c$ represent an optionally substituted methine group, $=N-$ or $-NH-$, either the bond $Z_a-Z_b$ or the bond $Z_b-Z_c$ being a double bond and the other bond a single bond; wherein at least $R^1$ or X or a substituent at a methine group represented by $Z_a$, $Z_b$ or $Z_c$ contains an ethylenically unsaturated polymerizable group, bonded to the coupler group through

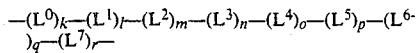

in which $L^0$ represents that part of the bond situated adjacent the coupler group while $L^7$ represents that part of the bond situated adjacent the ethylenically unsaturated group and in which $L^0$, $L^2$, $L^4$, $L^6$ (same or different) represent —O—, —NR—, —NRCO—, —CONR—, —NRSO$_2$—, —SO$_2$NR—, —COO—, —O—CO—, —NR—CO—NR—, —O—CO—NR—, —NR—COO— (with R=H or alkyl optionally substituted by carboxyl); $L^1$, $L^3$, $L^5$, $L^7$ (same or different represent alkylene, aralkylene, arylene, optionally substituted by carboxy; and k, l, m, n, o, p, q, r are each 0 or 1 with $l-m+n-o+p-q=0$; and wherein at least one of said $L^0$, $L^2$, $L^4$ and $L^6$ contains a nitrogen atom substituted with carboxy alkyl or at least one of the carbon atoms of said ethylenically unsaturated group is substituted with carboxyl or carboxy alkyl, and from 70 to 30% by weight of polymerized structural units of one or more monomers copolymerizable with said monomers of formula I and selected from the group consisting of esters and amides of arylic acid and derivatives thereof, vinylesters, acrylonitrile, methacrylonitrile, aromatic vinyl compounds, itaconic acid, citraconic acid, crotonic acid, acrylic acid, methacrylic acid, vinylidene chloride, vinylalkylethers, esters of maleic acid, N-vinyl-2-pyrrolidine, N-vinyl-pyridine, 2-vinyl-pyridine and 4-vinylpyridine.

* * * * *